US012678113B2

(12) United States Patent
Cai et al.

(10) Patent No.: US 12,678,113 B2
(45) Date of Patent: Jul. 14, 2026

(54) ROTARY IMAGING SYSTEM, PLANT IMAGER, ANIMAL IMAGER, AND ANIMAL AND PLANT IMAGER

(71) Applicant: CLINX SCIENCE INSTRUMENTS CO., LTD, Shanghai (CN)

(72) Inventors: Rongwei Cai, Shanghai (CN); Xiongqun Chen, Shanghai (CN); Huiming Wang, Shanghai (CN); Debao Chu, Shanghai (CN); Jie Gao, Shanghai (CN)

(73) Assignee: CLINX SCIENCE INSTRUMENTS CO., LTD, Shanghai (CN)

( * ) Notice: Subject to any disclaimer, the term of this patent is extended or adjusted under 35 U.S.C. 154(b) by 694 days.

(21) Appl. No.: 18/004,306

(22) PCT Filed: Jul. 13, 2021

(86) PCT No.: PCT/CN2021/106063
§ 371 (c)(1),
(2) Date: May 8, 2023

(87) PCT Pub. No.: WO2022/012545
PCT Pub. Date: Jan. 20, 2022

(65) Prior Publication Data
US 2023/0263490 A1 Aug. 24, 2023

(30) Foreign Application Priority Data
Jul. 14, 2020 (CN) .......................... 202010683375.8

(51) Int. Cl.
*G02B 7/18* (2021.01)
*A61B 5/00* (2006.01)
(Continued)

(52) U.S. Cl.
CPC .......... *A61B 6/4476* (2013.01); *A61B 5/0035* (2013.01); *A61B 5/0059* (2013.01);
(Continued)

(58) Field of Classification Search
CPC ... A61B 6/4476; A61B 5/0035; A61B 5/0059; A61B 6/4417; A61B 6/508;
(Continued)

(56) References Cited

U.S. PATENT DOCUMENTS

| | | | |
|---|---|---|---|
| 2004/0096029 A1 | 5/2004 | Shiota et al. | |
| 2008/0118023 A1* | 5/2008 | Besson ................ | A61B 6/4216 |
| | | | 604/510 |

(Continued)

FOREIGN PATENT DOCUMENTS

| | | |
|---|---|---|
| CN | 204439546 U | 7/2015 |
| CN | 104939858 A | 9/2015 |

(Continued)

OTHER PUBLICATIONS

Oct. 19, 2021 International Search Report issued in International Patent Application No. PCT/CN2021/106063.
(Continued)

*Primary Examiner* — Uzma Alam
*Assistant Examiner* — Mamadou Faye
(74) *Attorney, Agent, or Firm* — Houston Beshining Law Office PLLC; Liangang Ye

(57) ABSTRACT

A rotary imaging system, a plant imager, an animal imager, and an animal and plant imager, relating to the technical field of living sample imaging. The plant imager, the animal imager, and the animal and plant imager all comprise a rotary imaging system. The rotary imaging system comprises the sample table unit is used for carrying a sample; the camera unit is used for imaging the sample; the rotation unit comprises an accommodating cavity accommodating the
(Continued)

sample table unit, and the rotation unit is used for driving the camera unit to rotate with respect to the sample table unit and controlling the camera unit to be stationary with respect to the sample table unit. By means of rotary imaging system, powerful data support is provided for the subsequent image reconstruction and image fusion, and the number of cameras required for imaging different parts of a sample is also reduced.

20 Claims, 8 Drawing Sheets

(51) Int. Cl.

| | | |
|---|---|---|
| *A61B 6/00* | (2006.01) | |
| *A61B 6/50* | (2024.01) | |
| *G01N 21/64* | (2006.01) | |
| *G01N 23/04* | (2018.01) | |
| *G01N 23/083* | (2018.01) | |
| *A61B 6/04* | (2006.01) | |

(52) U.S. Cl.
CPC ............ *A61B 6/4417* (2013.01); *A61B 6/508* (2013.01); *G01N 21/6456* (2013.01); *G01N 23/04* (2013.01); *G01N 23/083* (2013.01); *A61B 6/0407* (2013.01); *G01N 2223/3306* (2013.01)

(58) Field of Classification Search
CPC . A61B 6/0407; A61B 2503/40; A61B 5/0071; A61B 5/0077; A61B 5/704; A61B 6/04; A61B 6/42; G01N 21/6456; G01N 23/04; G01N 23/083; G01N 2223/3306; G01N 23/046; G01N 21/01; G01N 21/763; G01N 2021/6419; G01N 2021/6482; G01N 2021/8466; G01N 21/84; G02B 7/18; G02B 7/1815; G02B 26/0816
See application file for complete search history.

(56) References Cited

U.S. PATENT DOCUMENTS

| | | | |
|---|---|---|---|
| 2011/0303851 | A1 | 12/2011 | Tybinkowski |
| 2012/0001070 | A1 | 1/2012 | Takagi |
| 2013/0136441 | A1* | 5/2013 | Yamada .................. G03B 19/12 |
| | | | 396/447 |
| 2014/0046212 | A1 | 2/2014 | Deutschmann |
| 2014/0191138 | A1 | 7/2014 | Atzler et al. |
| 2016/0377545 | A1* | 12/2016 | Wang .................. G01N 21/6456 |
| | | | 250/459.1 |
| 2017/0333142 | A1 | 11/2017 | Itkowitz et al. |
| 2018/0070900 | A1 | 3/2018 | Fortuna et al. |
| 2018/0165820 | A1* | 6/2018 | Rhodes, Jr. ............ G01N 21/01 |
| 2018/0177473 | A1* | 6/2018 | Gregerson ........... A61B 6/0407 |

FOREIGN PATENT DOCUMENTS

| | | |
|---|---|---|
| CN | 107709968 A | 2/2018 |
| CN | 209048162 U | 7/2019 |
| CN | 212261346 U | 1/2021 |

OTHER PUBLICATIONS

Oct. 19, 2021 Written Opinion of the International Searching Authority issued in International Patent Application No. PCT/CN2021/106063.
Chinese Patent Priority Application No. 202010683375.8.
Apr. 14, 2023 First Office Action issued in Indian Patent Application No. 202347008860.
Dec. 5, 2023 Supplementary European Search Report issued in European Patent Application No. 21842005.7.
Dec. 15, 2023 First Office Action issued in European Patent Application No. 21842005.7.
Apr. 1, 2025 Hearing Notice issued in Indian Patent Application No. 202347008860.
Sep. 16, 2025 First Office Action issued in Chinese Patent Application No. 202010683375.8.
Sep. 12, 2025 Chinese Search Report issued in Chinese Patent Application No. 202010683375.8.
Jan. 8, 2026 Rejection Decision issued in Chinese Patent Application No. 202010683375.8.

* cited by examiner

ROTARY IMAGING SYSTEM, PLANT IMAGER, ANIMAL IMAGER, AND ANIMAL AND PLANT IMAGER

This application is a National Stage of International Application No. PCT/CN2021/106063, filed on Jul. 13, 2021, which claims the priority of Chinese patent application 2020106833758 with a filing date of Jul. 14, 2020. The contents of the Chinese patent application are incorporated herein by reference in their entireties.

TECHNICAL FIELD

The present disclosure relates to the technical field of living sample imaging, in particular to a rotary imaging system, a plant imager, an animal imager and an animal and plant imager.

BACKGROUND

Living imaging technology applies imaging methods to non-invasively and quickly observe the optical signals of living bodies, and makes qualitative and quantitative research on biological processes in living bodies at the cellular and molecular levels, which plays an important role in promoting the development of disease biology, early detection, nature determination, evaluation and treatment of diseases.

In the existing living imaging technology, a sample table carries a sample, and the sample is imaged through multiple cameras, and by adjusting the relative position relationship between the sample table and the camera, the sample at different positions is imaged, which provides image information for further operations of two-dimensional reconstruction of images, three-dimensional reconstruction of images and three-dimensional fusion of multi-channel images.

At present, the sample table is driven by a three-axis motion mechanism to achieve translation or rotation in three directions of X, Y, and Z perpendicular to each other, or multiple cameras image the sample at different positions to obtain the image information of the sample at different positions. However, it is easy to cause the sample to slide during the actual movement of the sample table, which makes the finally obtained image information deviate from the initial expected image. In addition, the scheme of using multiple cameras will greatly increase the system cost.

CONTENT OF THE PRESENT INVENTION

The technical problem to be solved by the present disclosure is to provide a rotary imaging system, a plant imager, an animal imager, and an animal and plant imager in order to overcome the above-mentioned defects in the prior art.

The present disclosure solves the above technical problems through the following technical solutions:

a rotary imaging system, comprising:

a sample table unit which is used for carrying a sample;

a camera unit which is used for imaging the sample; and, a rotation unit, the rotation unit includes an accommodating cavity accommodating the sample table unit, the rotation unit is used for driving the camera unit to rotate with respect to the sample table unit, and controlling the camera unit to be stationary with respect to the sample table unit.

Preferably, the rotation unit includes a rotation module and a power module, the power module is used for driving the rotation module to rotate with respect to the sample table unit; the rotation module is provided with the accommodating cavity, and the camera unit is fixedly connected to the rotation module.

In this solution, the rotation module is driven to rotate by the power module to control the rotation of the camera unit with respect to the sample, thereby adjusting the imaging angle of the camera unit when the sample does not move, thereby improving the flexibility of the imaging angle for imaging the sample and the accuracy of the image information obtained.

Preferably, the rotation module includes:

a rotary support assembly, the rotary support assembly is provided with the accommodating cavity, and the camera unit is installed on the rotary support assembly;

a circular guide rail, both ends of the rotary support assembly are fixedly connected to the circular guide rail; and, a guide assembly, the guide assembly is used for guiding the circular guide rail, and making the circular guide rail be located on a preset circular track.

In this solution, the camera unit is carried by the rotary support assembly, the circular guide rails are respectively fixed at both ends of the rotary support assembly, and the movement path of the circular guide rail is restricted by the guide assembly, thereby improving the stability of the rotary support assembly during movement.

Preferably, the guide assembly includes several pulleys, and each of the pulleys in the same guide assembly is evenly distributed along a virtual circle, and the pulleys guide the circular guide rail so that the circular guide rail is located on the preset circular track.

In this solution, the circular guide rail is guided by the pulley, and the rolling friction between the pulley and the circular guide rail reduces the mechanical loss when the circular guide rail moves.

Preferably, each guide assembly is provided with 6 pulleys to improve the stability of the rotary support assembly; and/or, the guide assembly guides an outer ring and/or the outer ring of the circular guide rail.

Preferably, the rotary support assembly includes a connecting piece, both ends of the connecting piece are fixedly connected to the circular guide rail, and the camera unit is installed on the connecting piece; wherein:

the rotary support assembly is provided with several plate-shaped connecting pieces, each of the connecting pieces is arranged at intervals along the circumferential direction of the circular guide rail, and each connecting piece surrounds to form the accommodating cavity; or, the rotary support assembly is provided with several circular connecting pieces, each connecting piece is arranged at intervals along the axial direction of the circular guide rail, adjacent connecting pieces are connected, and the middle part of each connecting piece forms the accommodating cavity, and connecting pieces located at two ends are fixedly connected with the circular guide rail; or, the rotary support assembly is provided with one connecting piece, and the connecting piece is provided with the accommodating cavity.

Preferably, the circular guide rail includes a guide rail part and a connecting part; the connecting part is in a shape of an annular plate or a cylinder; the inner ring and/or outer ring of the connecting part is provided with the guide rail part; the rotary support assembly is fixedly connected to the connecting part; and/or,

the circular guide rail includes a transmission gear part, the transmission gear part meshes with the power module, and the power module makes the circular guide rail rotate by driving the transmission gear part.

Preferably, the power module includes a power element for outputting a torque and a gear set, an input end of the gear set is fixedly connected to an output end of the power element, and an output end of the gear set meshes with the rotation module.

Preferably, the camera unit includes a first imaging module and a second imaging module both arranged on the rotation unit; when the first imaging module performs imaging, a light emitted, excited and reflected by the sample enters the first imaging module through a first optical path; when the second imaging module performs imaging, the light emitted, excited and reflected by the sample enters the second imaging module through the first optical path.

In this solution, the camera unit can realize imaging of multiple wave bands or modes through any one of the first imaging module and the second imaging module. The first imaging module and the second imaging module share the first optical path, so that images of different wave bands or modes captured by the first imaging module and the second imaging module can be directly subjected to image fusion processing.

Preferably, the first imaging module includes a first camera and a first mirror both arranged on the rotation unit, and the second imaging module includes a second camera and a second mirror both arranged on the rotation unit;

when the first imaging module performs imaging, the second mirror is located at a first position, and the light emitted, excited and reflected by the sample enters the first mirror through the first optical path, and is reflected into the first camera by the first mirror;

when the second imaging module performs imaging, the second mirror is located at a second position, and the light emitted, excited and reflected by the sample enters the second mirror through the first optical path, and is reflected into the second camera by the second mirror.

In this solution, by adjusting the position of the second mirror with respect to the first optical path, the first imaging module and the second imaging module share the first optical path.

Preferably, the second imaging module further includes a swinging component, and the swinging component includes:

a swing bracket, the swing bracket is rotatably connected with the second camera, and the second mirror is fixedly connected to the swing bracket;

a first sliding assembly, the first sliding assembly is fixedly connected to the swing bracket, and tan output end of the first sliding assembly is slidably connected to the swing bracket; and, a first linear mechanism, the first linear mechanism is fixedly connected to the rotation unit, an output end of the first linear mechanism is rotatably connected to the output end of the first sliding assembly; the output end of the first linear mechanism outputs a linear motion, driving the output end of the first slide assembly to slide with respect to the swing bracket, and causing the swing bracket to swing.

In this solution, the linear motion output by the first linear mechanism drives the swing bracket to swing with respect to the first optical path or the first camera, thereby realizing the swing of the second mirror.

Preferably, the camera unit further includes:

an X-ray imaging module, the X-ray imaging module includes an X-ray light source for emitting an X-ray and an X-ray detector, the X-ray detector is set to remain relatively stationary with the sample table unit, and when the X-ray imaging module performs imaging, the second mirror is located at the first position, the X-ray propagates along the first optical path, and the X-ray detector absorbs the X-ray passing through the sample and converts the X-ray into image information; and, a synchronous motion driving part, the synchronous motion driving part is fixedly connected to the rotation unit and used for driving the X-ray light source and the first imaging module to move synchronously.

Preferably, the synchronous motion driving part includes:

a mounting bracket, the mounting bracket is fixedly connected to the rotation unit, and the X-ray light source, the first camera and the first mirror are all fixedly connected to the mounting bracket; and, a second linear mechanism, the second linear mechanism is connected to the rotation unit and used for driving the mounting bracket to move in a horizontal direction.

In this solution, the second linear mechanism drives the mounting bracket to realize the movement of the X-ray light source, the first camera and the first mirror, so as to realize the adjustment of the positional relationship between the X-ray light source and the first camera with respect to the first optical path, and further realize that the X-ray imaging source and the first imaging source share the first optical path. Preferably, the second linear mechanism includes:

a second drive assembly, the second drive assembly is fixedly connected to the rotation unit and used for driving the mounting bracket to move linearly; and, a second sliding assembly, the second sliding assembly includes a second guide rail and a second slide block in one-to-one correspondence, the second guide rail is fixedly connected to the rotation unit, and the second slide block is slidably connected with the second guide rail and fixedly connected with the mounting bracket.

In this solution, the second sliding assembly is fixedly connected to the rotation unit, so as to transmit the force of the second linear mechanism to the rotation unit. The second drive assembly drives the mounting bracket to move, so as to realize the position of the X-ray light source, the first camera and the first mirror with respect to the first optical path.

Preferably, the camera unit further includes a third imaging module; the third imaging module includes a third camera based on visible light imaging, and the third camera is fixedly connected to the rotation unit and located in the accommodating cavity; the third camera is set to directly receive light emitted or reflected by the sample.

Preferably, the first camera is an infrared camera; and/or, the second camera is a bioluminescence camera or a fluorescence camera; and/or, the third camera is a CMOS camera; and/or, the camera unit includes a first light source for emitting a near-infrared laser, and when the first camera is imaging, the first light source illuminates the sample; and/or, the camera unit includes a second light source for emitting an excitation light, the second light source excites the sample to emit biological fluorescence, and the biological fluorescence enters the second imaging module through the first optical path for imaging; and/or, the camera unit includes a third light source for emitting a white light, and when the third camera forms is imaging, the third light source illuminates the sample.

Preferably, the rotary imaging system further includes a dark box unit, the dark box unit includes an inner box module located in the accommodating cavity, the inner box module is provided with a light-passing hole, and the light-passing hole is located on the first optical path, the sample table unit is located in the inner box module, and the light emitted, excited and reflected by the sample is incident to the outside of the inner box module through the light-passing hole.

In this solution, the influence of external light on imaging is reduced by placing the sample in the inner box module.

Preferably, the inner box module includes:

a rotary box, the rotary box is set to keep relatively stationary with the rotation unit, the rotary box is provided with the light-passing hole; and, a fixed box, the fixed box is rotatably connected with the rotary box and optically sealed; the sample table unit is fixedly connected to the fixed box, and penetrates into the rotary box.

In this solution, by setting the technical connection between the rotary box and the fixed box and the rotation unit, and setting the sample table unit to be fixedly connected to the fixed box and the camera unit to be connected to the rotary box, the positional relationship between the camera unit and the sample can be adjusted.

Preferably, the fixed box is a cylinder; and/or, the rotary box is a cylinder; and/or, the fixed box is provided with a temperature-controlled air inlet for communicating with outside and a temperature-controlled air outlet for communicating with the outside; and/or, the fixed box is provided with an anesthesia air inlet for communicating with the outside and an anesthesia air outlet for communicating with the outside; and/or, the fixed box is provided with a moisture air inlet for communicating with the outside and a moisture air outlet for communicating with the outside.

A plant imager, comprising a housing, the sample is a living plant, wherein the plant imager further comprises the imaging system according to any one of the above, and the rotation unit is connected to inner of the housing.

An animal imager, comprising a housing, the sample is a living animal, wherein the animal imager also comprises the imaging system as described in any one of the above, and the rotation unit is connected to inner of the housing.

An animal and plant imager, comprising a housing, the animal and plant imager has the functions of imaging a living animals and imaging a living plant; wherein the animal and plant imager also includes the imaging system as described in any one of the above, and the rotation unit is arranged inside the housing.

On the basis of conforming to common knowledge in the field, the above-mentioned preferred conditions can be combined arbitrarily to obtain preferred examples of the present disclosure.

The positive progressive effects of the present disclosure are:

In the present disclosure, the camera unit is controlled to rotate and stay still with respect to the sample table unit via the rotation unit. First, the camera unit is adjusted to different positions of the sample for imaging when the sample is not moving, so that the angle at which the camera unit images the sample is always accurate, and different cameras share the same optical path when shooting samples at the same angle, which is conducive to obtaining more accurate 3D reconstruction models and more accurate fusion images.

Secondly, the effect of imaging different positions of the sample is realized, and the positional relationship of the camera unit with respect to the sample table unit is relatively flexible, thereby reducing the number of cameras required to realize this function.

Thirdly, the imaging process does not involve the movement of the sample table unit, and the camera unit outputs rotational movement, so that the space occupied by adjusting the relative position of the camera unit and the sample is small, so that the imaging system has a more compact structure and a smaller volume.

Figure 1:
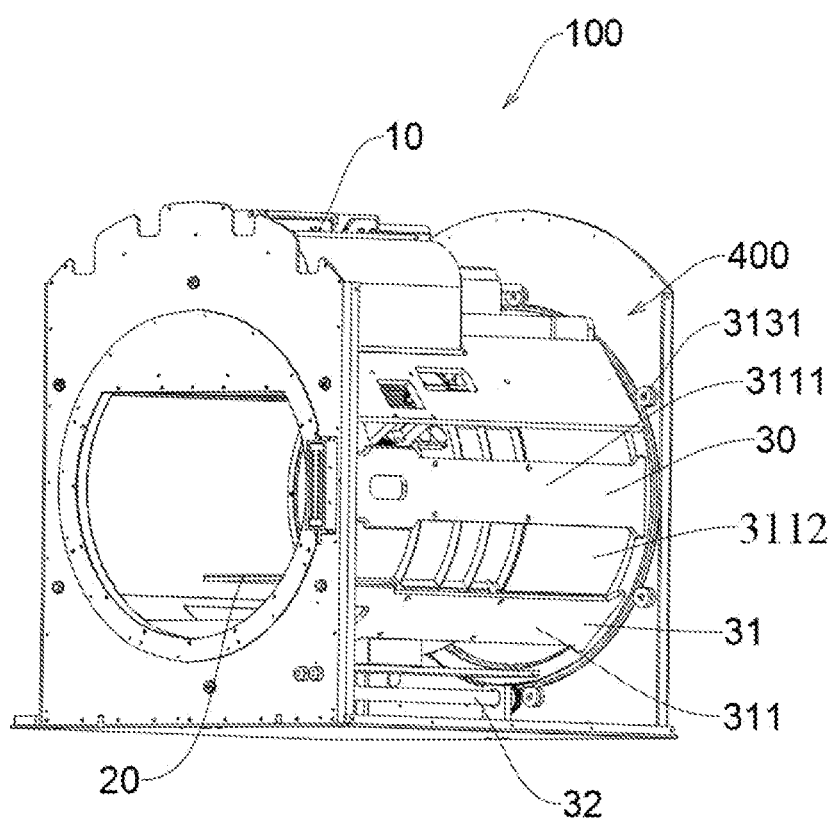
FIG. 1 is a structural diagram of an imaging system of an embodiment of the present disclosure.

DESCRIPTION OF REFERENCE NUMERALS imager 1000
imaging system 100
camera unit 10
first imaging module 11
first camera 111
first mirror 112
second imaging module 12
second camera 121
second mirror 122
first position 123
second position 124
swinging component 125
swing bracket 1251
first linear mechanism 1252
first drive assembly 1253
first transmission assembly 1254
first screw 1255
first nut 1256
first sliding assembly 1257 first guide rail 1258
first slide block 1259
connecting frame 12510
first bending part 12511
second bending part 12512
camera base 126
X-ray imaging module 13
X-ray light source 131
X-ray detector 132
synchronous motion driving part 14
mounting bracket 141
light source mounting part 142
mirror mounting part 143
first camera mounting part 144
second linear mechanism 145
second drive assembly 146
second sliding assembly 147
second guide rail 148
second slide block 149
fixed bracket 15
second camera mounting part 151
third imaging module 16
third camera 161
first light source 171
second light source 172
third light source 173
sample table unit 20; sample table 210
rotation unit 30
rotation module 31
rotary support assembly 311
connecting piece 3111
accommodating cavity 3112
circular guide rail 312
guide rail part 3121
guide rail surface 31211
connecting part 3122
transmission gear part 3123
guide assembly 313
pulley 3131
power module 32
power element 321
gear set 322
driving wheel 3221
driven wheel 3222
drive wheel 3223
inner box module 40
imaging room 41
rotary box 42
fixed box 43
temperature-controlled air inlet 431
temperature-controlled air outlet 432
humidifier 433
anesthesia air outlet 434
sample 200
top of sample 201
first optical path 300
housing 400

DETAILED DESCRIPTION OF THE PREFERRED EMBODIMENT

The present disclosure is further illustrated below by means of embodiments, but the present disclosure is not limited to the scope of the following embodiments.

An embodiment of the present disclosure provides a rotary imaging system 100 for imaging a sample 200. The imaging system 100 of the embodiment of the present disclosure is used in an imager 1000, and the imaging system 100 is installed in a housing 400 of the imager 1000. For ease of understanding, the technical connection between the imaging system 100 and the housing 400 will be introduced accordingly in the process of explaining the structure of the imaging system 100 below.

Please refer to FIG. 1 for understanding. The imaging system 100 of the embodiment of the present disclosure includes a sample table unit 20, a camera unit 10, and a rotation unit 30; the sample table unit 20 is used for carrying the sample 200, comprising a sample table 210; the camera unit 10 is used for imaging the sample 200; the rotation unit 30 includes an accommodating cavity 3112 accommodating the sample table unit 20, and the rotation unit 30 is used for driving the camera unit 10 to rotate with respect to the sample table unit 20 and controlling the camera unit 10 to be stationary with respect to the sample table unit 20.

Herein, the sample 200 is located in the accommodating cavity 3112 together with the sample table unit 20. When imaging the sample 200 from a certain angle: the rotation unit 30 drives the camera unit 10 to rotate to a corresponding position and makes the camera unit 10 and the sample table unit 20 remain relatively stationary, and then the camera unit 10 directly images the sample 200 from this position or imaging is performed after further adjusting the positional relationship of the camera in the camera unit 10 with respect to the sample 200. It is certain that according to the requirement of imaging the sample 200, the rotation unit 30 can drive the camera unit 10 to rotate with respect to the sample 200 while imaging the sample 200.

It can be seen from the above that the imaging system 100 of the embodiment of the present disclosure controls the rotation and stationary of the camera unit 10 with respect to the sample table unit 20 via the rotation unit 30, realizing the function of adjusting the camera unit 10 to different positions of the sample 200 for imaging when the sample 200 is not moving. Since the sample table unit 20 does not move all the time, there is no relative sliding between the sample 200 and the sample table unit 20 during the entire imaging process, so the angle at which the camera unit 10 images the sample 200 is always accurate, and when subsequent image reconstruction and image fusion are performed based on accurate image information, the specific position of the studied sample 200 can be accurately located. For example, the imaging system 100 based on the embodiment of the present disclosure obtains accurate image information of an animal living body, and after subsequent processing of the image information, the location of tumor focus and drug action can be accurately located.

The imaging system 100 of the embodiment of the present disclosure realizes the function of imaging different positions of the sample 200 by adjusting the rotation of the camera unit 10 with respect to the sample table unit 20. The positional relationship of the camera unit 10 with respect to the sample table unit 20 is relatively flexible, thus reducing the number of cameras required to perform this function. For example, when imaging different positions of a plant, the prior art is realized by multiple cameras, wherein at least one camera is located on the side of the plant to image the side view direction of the plant, while the imaging system 100 of the embodiment of the present disclosure only requires one camera to realize the function of imaging from the top and two sides of the plant respectively.

The imaging system 100 of the embodiment of the present disclosure controls the relative positional relationship of the camera unit 10 with respect to the sample table unit 20 through the rotation unit 30, so that the imaging angle of the sample 200 is more flexible and has a wider range. In addition, the imaging process does not involve the movement of the sample table unit 20, and the camera unit 10 outputs a rotational movement, so that the space occupied by adjusting the relative position of the camera unit 10 and the sample 200 is small, so that the imaging system 100 has a more compact structure and a smaller size.

Further, a first side and a second side are defined as two opposite sides of the sample table unit 20. The camera unit 10 is used for imaging the sample 200 from the first side of the sample 200, the top of the sample 201 and the second side of the sample 200, respectively. In this embodiment, the camera unit 10 can image the sample 200 from any angle of the first side of the sample 200, the top of the sample 201 and any angle of the second side of the sample 200. In other words, the rotation unit 30 controls the rotation angle of the camera unit 10 with respect to the sample table unit 20 to be greater than or equal to 180°.

Figure 2:
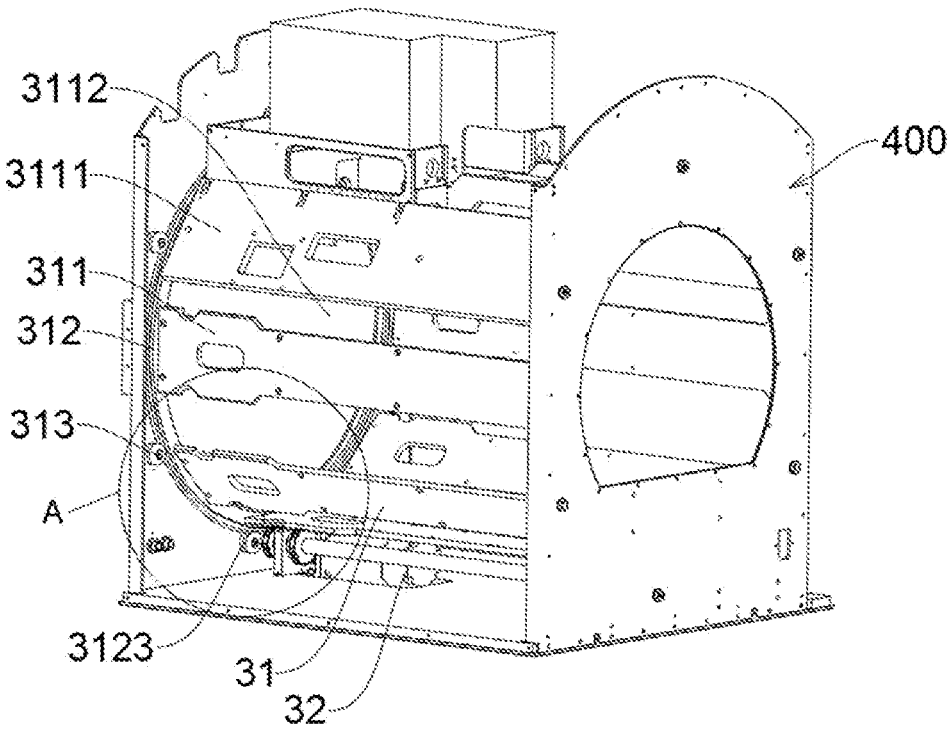
FIG. 2 is a structural diagram of the imaging system of an embodiment of the present disclosure.
Figure 3:
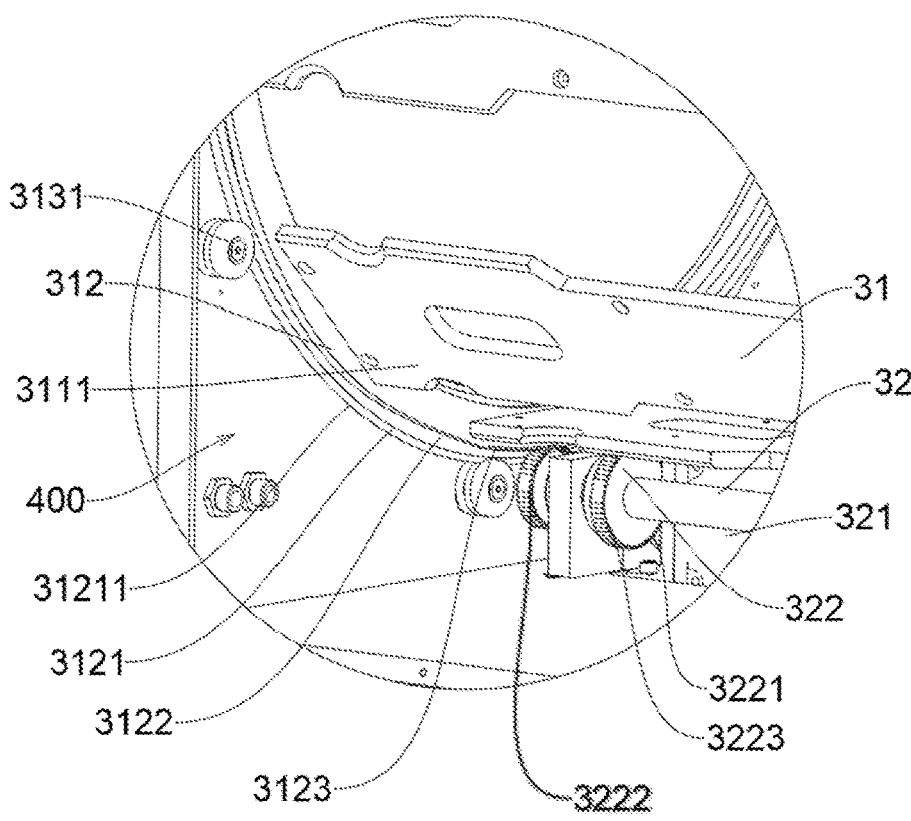
FIG. 3 is an enlarged view of part A of FIG. 2.

Please refer to FIGS. 2-3 for understanding. The rotation unit 30 includes a rotation module 31 and a power module 32, and the power module 32 is used for driving the rotation module 31 to rotate with respect to the sample table unit 20. The rotation module 31 is provided with the accommodating cavity 3112 mentioned above, and the camera unit 10 is fixedly connected to the rotation module 31. Herein, the power module 32 is fixed on the bottom of the housing 400, and the rotation module 31 is installed in the housing 400 and located above the power module 32.

In the imaging system 100 of this embodiment, the power module 32 is placed outside the rotation module 31. It is true that in other embodiments, as an alternative means, the power module 32 is internal to the rotation module 31, and can drive the rotation module 31 to rotate with respect to the sample table unit 20, which is also within the protection scope of the present disclosure.

Please refer to FIGS. 1-3 for understanding. The rotation module 31 includes a rotary support assembly 311, an circular guide rail 312, and a guide assembly 313; the rotary support assembly 311 is provided with the above-mentioned accommodating cavity 3112, that is, the sample 200 is located inside the rotary support assembly 311; the above-mentioned camera unit 10 is installed on the rotary support assembly 311; both ends of the rotary support assembly 311 are fixedly connected with the circular guide rail 312; the guide assembly 313 is used for guiding the circular guide rail 312, and making the circular guide rail 312 be located on a preset circular track.

Specifically, the guide assembly 313 is fixedly connected to the housing 400, the freedom of rotation of the circular guide rail 312 around its own axial rotation is released, and other freedom of rotation and freedom of each displacement are constrained by the guide assembly 313, wherein, the track of the circular guide rail 312 rotating around its axial direction is the preset circular track.

The imaging system 100 of the embodiment of the present disclosure constrains the movement track of the rotary support assembly 311 provided with the circular guide rail 312 through the guide assembly 313, thereby driving the camera unit 10 on the rotary support assembly 311 to move with respect to the sample table unit 20, so as to adjust the positional relationship of the camera unit 10 and the sample 200.

The rotary support assembly 311 includes a connecting piece 3111, both ends of the connecting piece 3111 are directly or indirectly fixedly connected to the circular guide rail 312, and the camera unit 10 is installed on the connecting piece 3111.

Please refer to FIGS. 1-3 for understanding. In this embodiment, the rotary support assembly 311 is provided with a plurality of connecting pieces 3111. Each connecting piece 3111 is plate-shaped, and each connecting piece 3111 is arranged at intervals along the circumferential direction of the circular guide rail 312, and each connecting piece 3111 jointly encloses the above-mentioned accommodating cavity 3112. The camera unit 10 is installed on one or more connecting pieces 3111.

In some other embodiments, as an alternative means, the rotary support assembly 311 is provided with a plurality of circular connecting pieces 3111, and each circular connecting piece 3111 is arranged at intervals along the axial direction of the circular guide rail 312, and the adjacent connecting pieces 3111 are directly or indirectly fixedly connected. Two connecting pieces 3111 at both ends are fixedly connected to the corresponding circular guide rails 312. The camera unit 10 is installed on one or more of the connecting pieces 3111.

In some other embodiments, as an alternative means, the rotary support assembly 311 is provided with only one connecting piece 3111, and the connecting piece 3111 is cylindrical or semi-cylindrical, and the wall of the connecting piece 3111 encloses the accommodating cavity 3112. The camera unit 10 is installed on the connecting piece 3111.

Please refer to FIGS. 1-3 for understanding. The guide assembly 313 includes several pulleys 3131, and each pulley 3131 in the same guide assembly 313 is evenly distributed along a virtual circle (not shown in the figure). The pulley 3131 guides the circular guide rail 312, and makes the circular guide rail 312 be located in the preset circular track. Specifically, the pulley 3131 is rotatably connected to the housing 400 through a fastener, and there is rolling friction between the circular guide rail 312 and the pulley 3131. It is true that in other embodiments, as an alternative means, the guide assembly 313 uses several slide blocks fixedly connected to the housing 400 to guide the circular guide rail 312, which is also within the protection scope of the present disclosure.

Please refer to FIGS. 1-2 for further understanding. Each guide assembly 313 is provided with at least three pulleys 3131. In this embodiment, each guide assembly 313 is provided with six pulleys 3131 as an example, so that the rotation module 31 has higher stability.

Please refer to FIGS. 1-3 for further understanding. In this embodiment, a guide rail surface 31211 is formed on the outer ring of the circular guide rail 312, and the guide assembly 313 is disposed on the outer ring of the circular guide rail 312, that is, each pulley 3131 guides the outer ring of the circular guide rail 312. It is true that in other embodiments, as an alternative means, a guide rail surface 31211 is formed on the inner ring of the ring guide rail 312, and the guide assembly 313 is arranged on the inner ring of its corresponding circular guide rail 312, that is, each pulley 3131 guides the inner ring of the annular guide rail 312, or, both the inner ring and the outer ring of the circular guide rail 312 are provided with guide rail surfaces 31211, and each guide rail surface 31211 corresponds to a guide assembly 313, both means are within the protection scope of the present disclosure.

The circular guide rail 312 includes a guide rail part 3121 and a connecting part 3122. The connecting part 3122 is in a shape of an annular plate or a cylinder, and the outer ring of the connecting part 3122 is provided with a guide rail part. The rotary support assembly 311 is fixedly connected to the connecting part 3122. Herein, the rotary support assembly 311 is directly or indirectly fixedly connected to the connecting part 3122 through the above-mentioned connecting plate, and a guiding relationship is formed between the guide rail part and the guide assembly 313.

Please refer to FIGS. 2-3 for understanding. In this embodiment, the outer ring of the connecting part 3122 is provided with a guide rail part. It is true that in other embodiments, as an alternative means, the inner ring of the connecting part 3122 is provided with a guide rail part, or both the inner ring and the outer ring of the connecting part 3122 are provided with guide rail parts, which are both within the protection scope of the present disclosure.

Please refer to FIGS. 2-3 for understanding. The circular guide rail 312 includes a transmission gear part 3123, and the transmission gear part 3123 meshes with the power module 32. The power module 32 rotates the circular guide rail 312 by driving the circular gear part, and finally realizes the adjustment of the positional relationship between the camera unit 10 and the sample 200. The transmission gear part 3123 is arranged around the circumferential direction of the circular guide rail 312. In different embodiments, the extension length of the transmission gear part 3123 may be different, and the transmission gear part 3123 may be a closed ring or an open semi-ring structure.

In this embodiment, the transmission gear part 3123 is arranged on the outer surface of the connecting part 3122. In other words, the outer ring of the connecting part 3122 is provided with both the guide rail part and the transmission gear part 3123. It is true that the guide rail part and the transmission gear part 3123 are staggered from each other in the axial direction of the circular guide rail 312.

Please refer to FIGS. 2-3 for understanding. The power module 32 includes a power element 321 for outputting a torque and a gear set 322. The input end of the gear set 322 is fixedly connected to the output end of the power element 321, and the output end of the gear set 322 meshes with the rotation module 31.

Specifically, the power element 321 is a motor, and the output end of the power element 321 is the output shaft of the motor. The gear set 322 includes several gears, and the effect of accelerating or decelerating is realized by setting the transmission ratio between the gears. It is certain that the gear set 322 may be replaced by a speed reducer in an embodiment that realizes the decelerating effect. In this embodiment, the gear set 322 includes a driving wheel 3221 and a driven wheel 3222. The driving wheel 3221 is the input end of the gear set 322, and is fixedly connected with the output shaft of the motor, and the driven wheel 3222 is the output end of the gear set 322, and is meshed with the transmission gear part 3123. The power element 321 drives the driving wheel 3221 to rotate, and directly or indirectly drives the driven wheel 3222 to rotate, which further makes the transmission gear part 3123 rotate. The gear set 322 in this embodiment further includes a drive wheel 3223, which is located between the driving wheel 3221 and the driven wheel 3222 and is used for outputting the rotational speed of the driving wheel 3221 to the driven wheel 3222.

Figure 4:
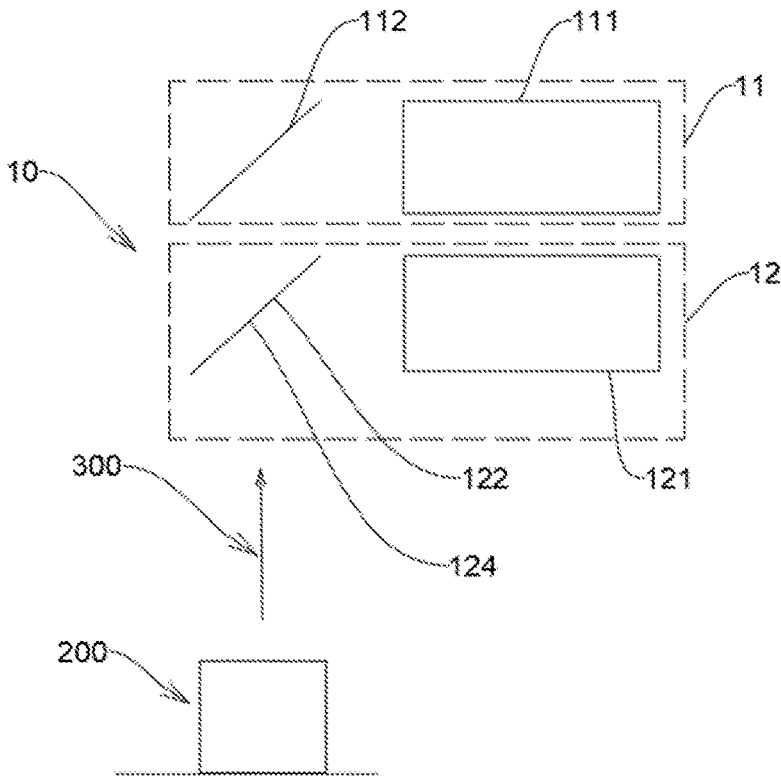
FIG. 4 is a schematic diagram of the principle of the second imaging module of the camera unit imaging a sample in an embodiment of the present disclosure.
Figure 5:
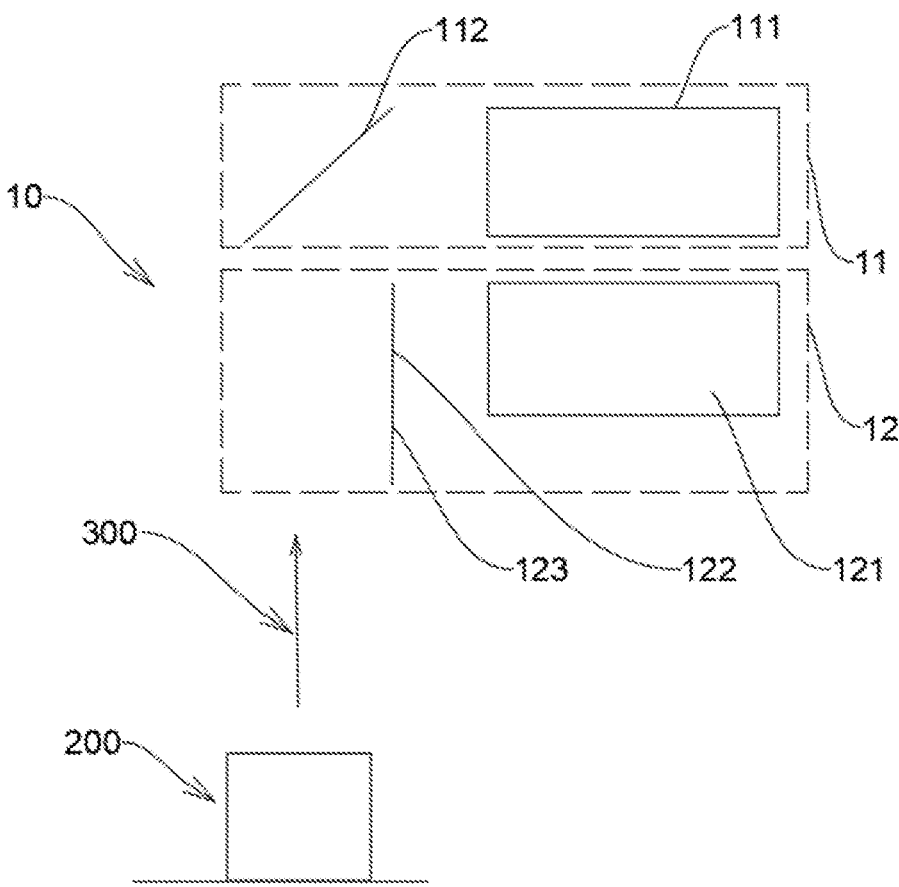
FIG. 5 is a schematic diagram of the principle of the first imaging module of the camera unit imaging a sample in an embodiment of the present disclosure.

Please refer to FIGS. 4-5 for understanding. The camera unit 10 includes a first imaging module 11 and a second imaging module 12 which are both arranged on the rotation unit 30. When the first imaging module 11 performs imaging, the light emitted, excited and reflected by the sample 200 enters the first imaging module 11 through the first optical path 300. When the second imaging module 12 performs imaging, the light emitted, excited and reflected by the sample 200 directly enters the second imaging module 12 through the first optical path 300.

Herein, the first imaging module 11 is located above the second imaging module 12. Both the first imaging module 11 and the second imaging module 12 are arranged on the rotary support assembly 311. Further, in this embodiment, the first imaging module 11 and the second imaging module 12 are both arranged on the connecting piece 3111.

On the one hand, the imaging system 100 can use one imaging module to realize imaging of multiple wave bands or modes. On the other hand, in the imaging system 100 of the embodiment of the present disclosure, the first imaging module 11 and the second imaging module 12 image the sample 200 separately. Both the first imaging module 11 and the second imaging module 12 receive the light emitted, excited or reflected by the sample 200 via the first optical path 300, then on the one hand, the first imaging module 11 and the second imaging module 12 can realize imaging of multiple wave bands or modes, and because the first optical path 300 is shared, it is more conducive to image fusion processing of images of different wave bands or modes captured; on the other hand, the first imaging module 11 and the second imaging module 12 jointly adjust their positional relationship with the sample 200 through the rotation module 31, so as to reduce the space occupied by the imaging system 100 and improves the compactness of the imaging system 100.

Please refer to FIGS. 4-5 for understanding. The first imaging module 11 includes a first camera 111 and a first mirror 112 both disposed on the rotation unit 30, and the second imaging module 12 includes a second camera 121 and a second mirror 122 both disposed on the rotation unit 30. When the first imaging module 11 performs imaging, the second mirror 122 is located at the first position 123, and the light emitted, excited or reflected by the sample 200 is reflected into the first mirror 112 through the first optical path 300, and is reflected by the first mirror 112 into the first camera 111; when the second imaging module 12 performs imaging, the second mirror 122 is located at the second position 124, and the light emitted, excited or reflected by the sample 200 enters the second mirror 122 through the first optical path 300, and is reflected by the second mirror 122 into the second camera 121.

Specifically, when the first imaging module 11 performs imaging, the second mirror 122 is arranged at the first position 123 avoiding the first optical path 300, so that light directly enters the first mirror 112. FIG. 5 shows a schematic view of a situation of the first position 123. When the second imaging module 12 performs imaging, the second mirror 122 is arranged on the first optical path 300, as shown in FIG. 4, so that light directly enters the second mirror 122. By adjusting the position of the second mirror 122 with respect to the first optical path 300, the first imaging module 11 and the second imaging module 12 share the first optical path 300, further enabling the first imaging module 11 and the second imaging module 12 to be closely overlapped in the up and down direction.

For further understanding, please refer to FIGS. 4-5. In FIGS. 4-5, the straight line containing an arrow shows the incident direction of the light from the sample 200, and the space occupied by the light propagating to the first mirror 112 and the second mirror 122 is the first optical path 300; it should be noted that the position of the first optical path 300 varies with the relative positions of the camera unit 10 and the sample 200. The first position 123 and the second position 124 of the second mirror 122 are briefly illustrated in FIGS. 4-5. The positional relationship between the second mirror 122 and the second camera 121 in the figures is not taken as a limitation on the protection scope of the present disclosure, and the second mirror 122 is within the protection scope of the present disclosure as long as it reflects light into the second camera 121 when the second imaging module 12 images and avoids the first optical path 300 when the first imaging module 11 images. FIGS. 4-5 is only used as a simple schematic of the working principle of the imaging system 100, which does not reflect the connection relationship between the second mirror 122 and the second camera 121. In FIGS. 4-5, the first camera 111 and the first mirror 112 are framed in a space with a dashed frame and the first imaging module 11 is illustrated, and the second camera 121 and the second mirror 122 are framed in a space with a dashed frame and the second imaging module 12 is illustrated. It should be noted that the two dashed frames here do not represent physical components.

The present disclosure does not limit whether the types of the first camera 111 and the second camera 121 are the same. In some embodiments, the first camera 111 and the second camera 121 are cameras of the same type, and in other embodiments, the first camera 111 and the second camera 121 are cameras of different types.

In the imaging system 100 of this embodiment, the first camera 111 and the second camera 121 are different types of cameras, on the one hand, it is convenient to realize different imaging requirements of the sample 200, on the other hand, different types of cameras are used for imaging the same sample 200, which is convenient for subsequent image fusion. The first camera 111 is an infrared camera, and the second camera 121 is a bioluminescence camera or a fluorescence camera, wherein the bioluminescence camera is interpreted as a camera that performs imaging based on bioluminescence, and the fluorescence camera is interpreted as a camera that performs imaging based on fluorescence. Specifically, the second camera 121 is a CCD camera or a SCMOS camera, and these two types of cameras have the functions of imaging bioluminescence and imaging fluorescence.

Figure 6:
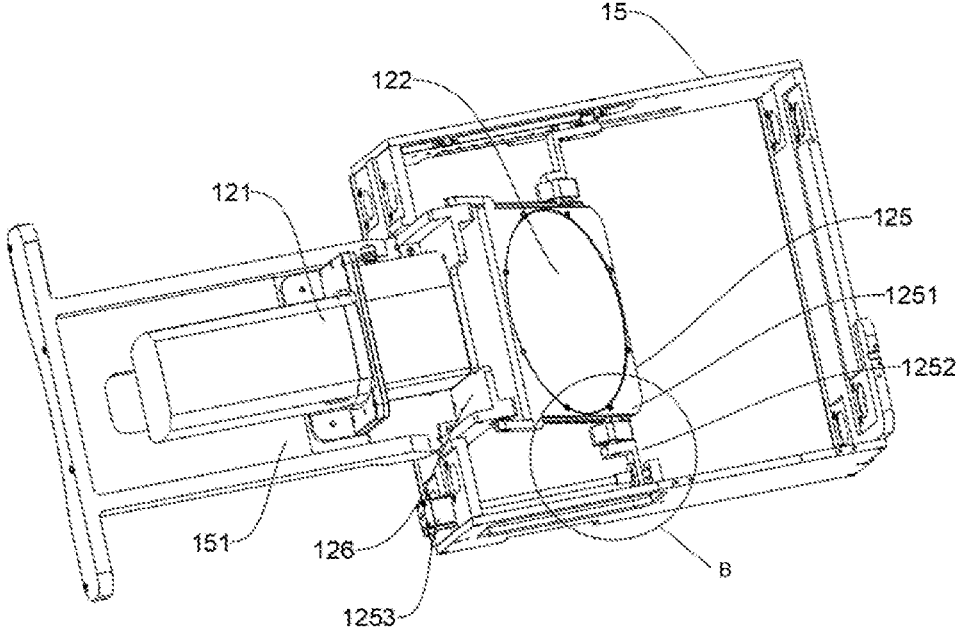
FIG. 6 is a structural diagram of a camera unit in an embodiment of the present disclosure, wherein a first camera and a first mirror are hidden.
Figure 7:
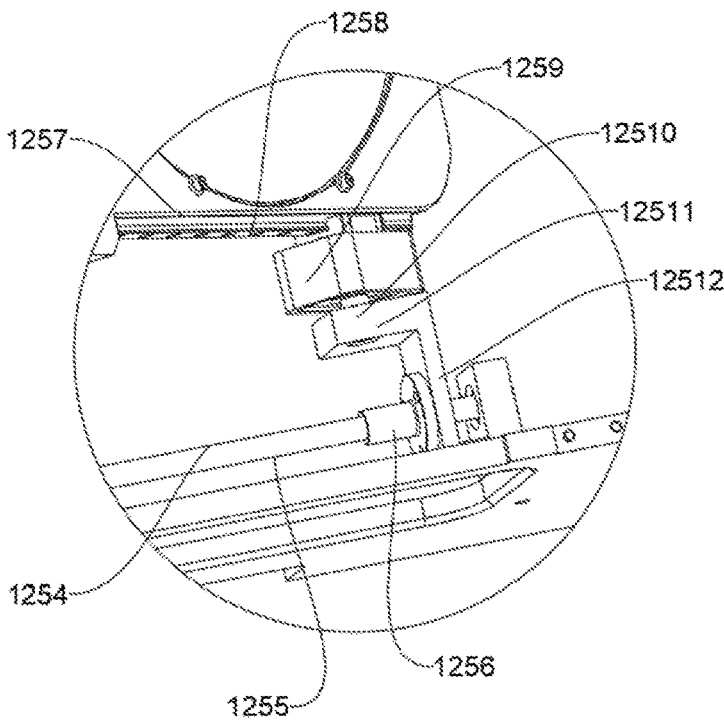
FIG. 7 is an enlarged view of part B of FIG. 6.
Figure 8:
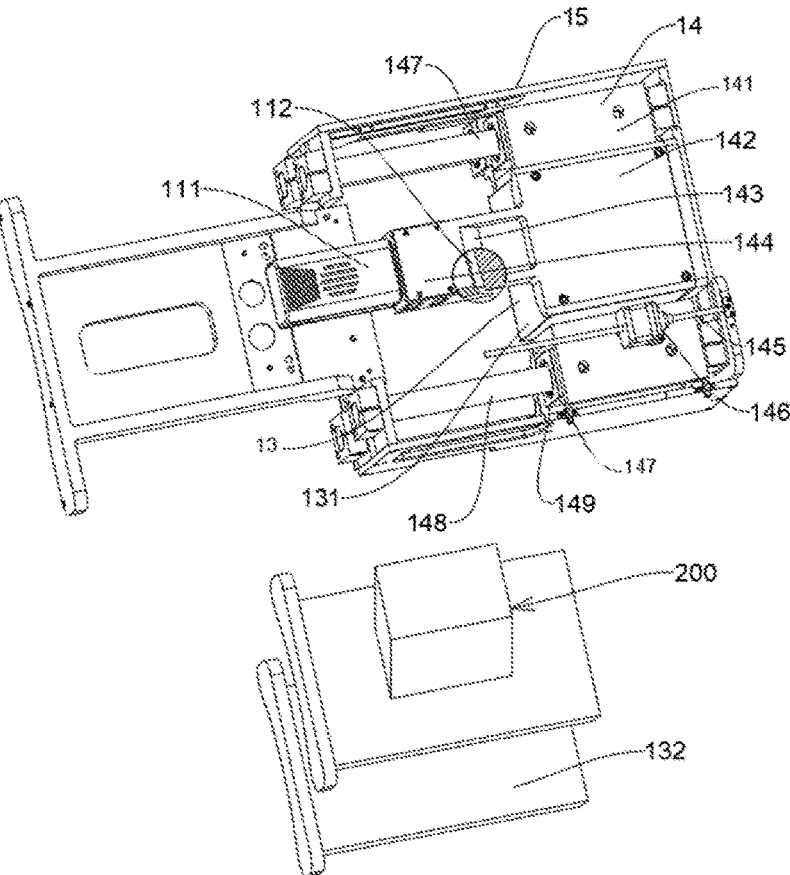
FIG. 8 is a structural diagram of the camera unit in an embodiment of the present disclosure, wherein a second camera and a second mirror are hidden.

Please refer to FIGS. 6-8 for understanding. In this embodiment, the camera unit 10 further includes a fixed bracket 15, and the fixed bracket 15 is fixed on a connecting piece 3111. The first camera 111, the first mirror 112, the second camera 121 and the second mirror 122 are all installed on the fixed bracket 15. The technical connection between the camera unit 10 and the fixed bracket 15 will be further described in the following process of unfolding each part of the camera unit 10.

Please refer to FIGS. 6-8, the second imaging module 12 also includes a swinging component 125, which is fixed on the fixed bracket 15 by means of a fastener. The swinging component 125 drives the second mirror 122 to swing with respect to the second camera 121, and switches between the first position 123 and the second position 124. In other words, the second mirror 122 switches between the first position 123 and the second position 124 through a swing action, and the swing force of the second mirror 122 is provided through the swinging component 125.

In this embodiment, the relative position between the second mirror 122 and the first optical path 300 is controlled by the swinging component 125, and at the same time, the control of the angle between the second mirror 122 and the second camera 121 is also realized. The motion amplitude of the second mirror 122 is small and the second mirror 122 occupies less space, and the structure of the second imaging module 12 is more compact. It is true that in other embodiments, as an alternative means, the angle between the second mirror 122 and the second camera 121 is always fixed, and the relative position between the second mirror 122 and the first optical path 300 is controlled by a mechanism that outputs linear reciprocating motion, which is also within the protection scope of the present disclosure.

Please refer to FIGS. 6-8, the swinging component 125 includes a swing bracket 1251, a first sliding assembly 1257 and a first linear mechanism 1252. The swing bracket 1251 is rotatably connected to the second camera 121, and the second mirror 122 is fixedly connected to the swing bracket 1251. The first sliding assembly 1257 is fixedly connected to the swing bracket 1251, and the output end of the first sliding assembly 1257 is slidably connected to the swing bracket 1251. The first linear mechanism 1252 is fixedly connected to the rotation unit 30. The output end of the first linear mechanism 1252 is rotatably connected to the output end of the first sliding assembly 1257, and the output end of the first linear mechanism 1252 outputs linear reciprocating motion, and drives the output end of the first sliding assembly 1257 to slide with respect to the swing bracket 1251 and makes the swing bracket 1251 swing.

Specifically, the swing bracket 1251 is rotatably connected to a camera base 126 through a fastener, and the second mirror 122 is fixed on the swing bracket 1251 so as to swing together with the swing bracket 1251. The mirror surface of the second mirror 122 faces the lens of the second camera 121 so as to reflect light into the second camera 121.

In this embodiment, the top of the swing bracket 1251 is connected to the camera base 126 through a rotating shaft. It is true that in other embodiments, as an alternative means, it is also within the protection scope of the present disclosure to set other positions of the swing bracket 1251 to be rotatably connected with the second camera 121 or the camera base 126. The first linear mechanism 1252 is installed on the fixed bracket 15 through a fastener, and the output end of the first linear mechanism 1252 drives the output end of the first sliding assembly 1257 to slide with respect to the swing bracket 1251 through outputting a linear motion, so that the swing bracket 1251 drives the second mirror 122 to rotate with respect to the second camera 121.

The imaging system 100 of this embodiment realizes the adjustment of the positional relationship between the second mirror 122 and the first optical path 300 via the swing bracket 1251, the first sliding assembly 1257 and the first linear mechanism 1252. It is true that in other embodiments, using other mechanisms to directly push the second mirror 122 to swing around the second camera 121 is also within the protection scope of the present disclosure.

Please refer to FIGS. 6-7 for further understanding. In this embodiment, the first sliding assembly 1257 is arranged on the side of the swing bracket 1251. It is true that in other embodiments, as an alternative means, the first sliding assembly 1257 is arranged on the surface of the swing bracket 1251 facing the second camera 121 or away from the second camera 121, which is also within the scope of protection of the disclosure.

Please refer to FIGS. 6-7 for further understanding. In this embodiment, the first sliding assembly 1257 and the first linear mechanism 1252 are only arranged on one side of the swing bracket 1251. It is true that in other embodiments, as an alternative means, both sides of the swing bracket 1251 are provided with a first sliding assembly 1257 and the first linear mechanism 1252, and each first linear mechanism 1252 act synchronously to jointly drive the swing bracket 1251 to swing, which is also within the protection scope of the present disclosure.

Please continue to refer to FIGS. 6-7. The first linear mechanism 1252 includes a first drive assembly 1253 and a first transmission assembly 1254. The first transmission assembly 1254 converts the rotary motion output by the first drive assembly 1253 into linear motion, and the output end of the first transmission assembly 1254 is slidably connected with the swing bracket 1251.

Herein, the first driving assembly 1253 is used as a power source for outputting rotational motion. The first drive assembly 1253 is installed on the fixed bracket 15 through a fastener, and the first transmission assembly 1254 is arranged in a form of cantilever on the fixed bracket 15, or is further slidably connected with the fixed bracket 15 while being fixed on the fixed bracket 15. In this embodiment, the first drive assembly 1253 is a motor. It is true that in other embodiments, as an alternative means, the first drive assembly 1253 adopts other components or mechanisms capable of outputting rotational motion, which is also within the protection scope of the present disclosure.

The input end of the first transmission assembly 1254 is fixedly connected with the output end of the first drive assembly 1253. The first transmission assembly 1254 converts received torque into linear motion.

In this embodiment, the first linear mechanism 1252 is realized based on the first drive assembly 1253 and the first transmission assembly 1254. It is true that in other embodiments, as an alternative means, the first linear mechanism 1252 can be directly realized via a screw stepping motor installed on the fixed bracket 15, and the output end of the screw stepping motor is slidably connected with the fixed bracket 15 and the swing bracket 1251.

Please continue to refer to FIGS. 6-7. The first transmission assembly 1254 includes a first screw 1255 and a first nut 1256, and one end of the first screw 1255 is fixedly connected to the first drive assembly 1253. The first nut 1256 and the first screw 1255 is threadedly fitted and slidably connected with the swing bracket 1251, and the first nut 1256 is also set to be slidably connected with the fixed bracket 15 to improve the stability of its movement. In other words, in this embodiment, the first drive assembly 1253 drives the first screw 1255 to rotate, and correspondingly, the first nut 1256 outputs linear motion, thereby driving the swing bracket 1251 to swing.

Please refer to FIG. 6 for further understanding. In this embodiment, the swinging component 125 further includes a first sliding assembly 1257, and the first sliding assembly 1257 includes a first guide rail 1258 and a first slide block 1259. The first guide rail 1258 is fixedly connected to the swing bracket 1251, the first slide block 1259 is slidably arranged with the first guide rail 1258, and the first slide block 1259 is rotatably connected to the output end of the first transmission assembly 1254.

Herein, the first guide rail 1258 is fixed on the side of the swing bracket 1251 by a fastener, and the first slide block 1259 corresponds to the first guide rail 1258 one by one. The first slide block 1259 and the first nut 1256 are rotatably connected through a connecting frame 12510, and the connecting frame 12510 is bent and is provided with a first bending part 12511 and a second bending part 12512. The first slide block 1259 and the first bending part 12511 are rotatably connected by a bearing, and the first nut 1256 is fixedly connected to the second bending part 12512.

Figure 9:
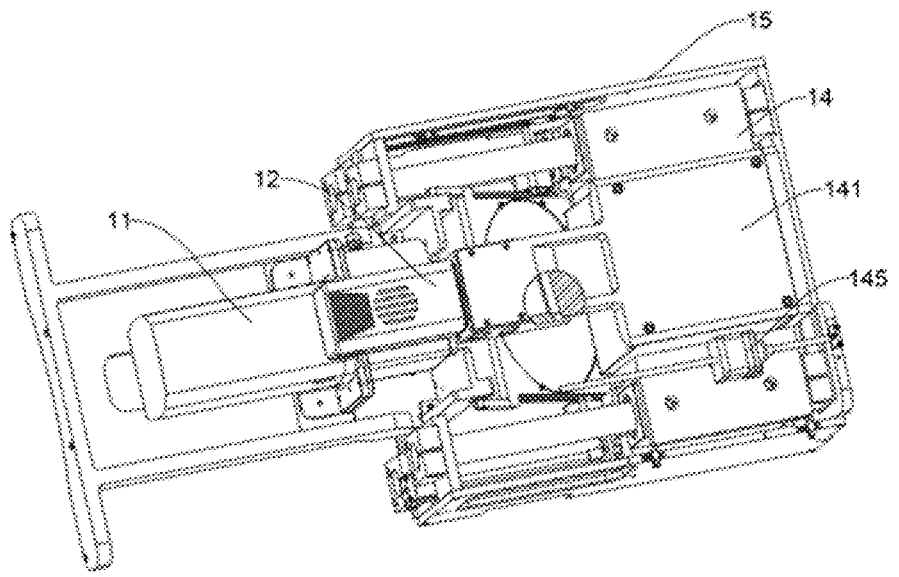
FIG. 9 is a structural diagram of the camera unit in an embodiment of the present disclosure, wherein the second mirror is located at a second position.

Please refer to FIGS. 8-9 for further understanding. The camera unit 10 also includes an X-ray imaging module 13 and a synchronous motion driving part 14. The X-ray imaging module 13 includes an X-ray light source 131 for emitting an X-ray. When the X-ray imaging module 13 performs imaging, the second mirror 122 is located at the first position 123, and the X-ray propagates along the first optical path 300. The synchronous motion driving part 14 is fixedly connected to the rotation unit 30 and used for driving the X-ray light source 131 and the first imaging module 11 to move synchronously in the horizontal direction.

In other words, the X-ray imaging module 13, the first imaging module 11 and the second imaging module 12 are independently imaging and share the first optical path 300. When the X-ray imaging module 13 performs imaging, the second mirror 122 swings to the first position 123, the X-ray light source 131 moves to the shooting position under the driving of the synchronous motion driving part 14, and the X-ray propagates along the first optical path 300; when the first imaging module 11 performs imaging, the first imaging module 11 moves to the shooting position under the driving of the synchronous motion driving part 14, so that the first mirror 112 is located on the first optical path 300. The synchronous motion driving part 14 outputs linear motion in the horizontal direction, and the output end of the synchronous motion driving part 14 forms a fixed connection with the X-ray light source 131 and the first imaging module 11, so as to realize synchronous control of the both.

Figure 11:
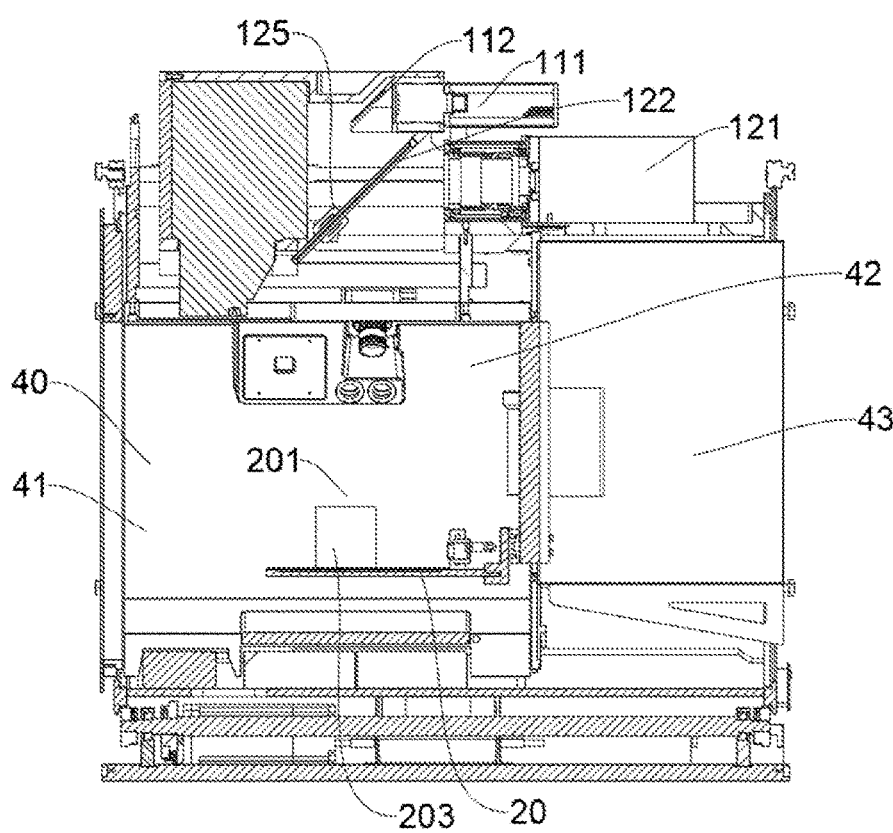
FIG. 11 is a structural diagram of the imaging system of an embodiment of the present disclosure.

Please refer to FIG. 11 for understanding. The X-ray imaging module 13 also includes an X-ray detector 132. The X-ray detector 132 is arranged to remain relatively stationary with the sample table unit 20, and is fixed below the sample 200. When the X-ray imaging module 13 performs imaging, the X-ray emitted by the X-ray light source 131 irradiates the sample 200 along the first optical path 300, and the X-ray detector 132 absorbs the X-ray transmitted through the sample 200 and converts the X-ray into image information.

Please refer to FIG. 7, the synchronous motion driving part 14 includes a mounting bracket 141 and a second linear mechanism 145. The mounting bracket 141 is fixedly connected to the rotation unit 30, and the X-ray light source 131, the first camera 111 and the first mirror 112 are all fixedly connected to the mounting bracket 141. The second linear mechanism 145 is connected to the rotation unit 30 and used for driving the mounting bracket 141 to move in the horizontal direction.

Specifically, the mounting bracket 141 is installed on the fixed bracket 15 and can move with respect to the fixed bracket 15. The mounting bracket 141 is a single plate, or a plate assembly formed by fixing several plates to each other. The mounting bracket 141 is at least used for integrating the X-ray light source 131, the first camera 111 and the first mirror 112 together. The mounting bracket 141 may only be connected to the output end of the second linear mechanism 145, or may be further slidably connected to the fixed bracket 15 on the basis of the connection with the output end of the second linear mechanism 145, so that the gravity of the X-ray light source 13, the first camera 111 and the first reflecting mirror 112 is transmitted to the fixed bracket 15, so as to improve the stability of the imaging system 100.

The second linear mechanism 145 is installed and fixedly connected to the fixed bracket 15 and can output horizontal movement. The mounting bracket 141 is connected to the output end of the second linear mechanism 145, so that the X-ray light source 131, the first camera 111, and the first mirror 112 move in the horizontal direction.

When the X-ray imaging module 13 performs imaging, and when the light outlet of the X-ray light source 131 is not on the first optical path 300, the second linear mechanism 145 drives the mounting bracket 141 to move, so that the light outlet of the X-ray light source 131 is aligned with the first optical path 300. When the first imaging module 11 performs imaging, and when the first mirror 112 is not on the first optical path 300, the second linear mechanism 145 drives the mounting bracket 141 to move, so that the first mirror 112 is on the first optical path 300.

The imaging system 100 of this embodiment realizes the effect that the X-ray imaging module 13 and the first imaging module 11 share the first optical path 300 for imaging through the mounting bracket 141 and the second linear mechanism 145, further improving the compactness of the imaging system 100, reducing the space occupied by the imaging system 100.

Please refer to FIG. 7, the second linear mechanism 145 includes a second drive assembly 146 and a second sliding assembly 147. The second drive assembly 146 is fixedly connected to the rotation unit 30 and is used for driving the linear movement of the mounting bracket 141.

Herein, the second drive component 146 is a screw stepping motor. The screw stepping motor is fixed on the fixed bracket 15, and the output end of the screw stepping motor is fixedly connected with the mounting bracket 141 so as to drive the mounting bracket 141 to move with respect to the fixed bracket 15. It is true that in other embodiments, as an alternative means, the second drive assembly 146 adopts the same structure as the first linear mechanism 1252, which is also within the protection scope of the present disclosure.

In this embodiment, the second sliding assembly 147 is located on the side of the X-ray light source 131. It is true that in other embodiments, the second sliding assembly 147 being located above or below the X-ray light source 131 is also within the protection scope of the present disclosure.

In this embodiment, two sides of the X-ray light source 131 are provided with second sliding assemblies 147, and each second sliding assembly 147 operates synchronously, improving the stability of movement of the X-ray light source 131, the first camera 111, the first mirror 112 and the mounting bracket 141. It is true that in other embodiments, only one side of the X-ray light source 131 is provided with a second sliding assembly 147, which is also within the protection scope of the present disclosure.

In this embodiment, each side of the X-ray light source 131 is respectively provided with two second sliding assemblies 147, and each second sliding assemblies 147 acts synchronously. It is true that in other embodiments, as an alternative means, it is also within the protection scope of the present disclosure to arrange a second sliding assembly 147 on one side of the X-ray light source 131.

The second sliding piece includes a second guide rail 148 and a second slide block 149 which are arranged in one-to-one correspondence. The second guide rail 148 is fixedly connected to the rotation unit 30, and the second slide block 149 is slidably connected to the second guide rail 148 and fixedly connected to the mounting bracket 141. The second sliding assembly 147 guides and supports for the mounting bracket 141 and the components fixed on the mounting bracket 141. Both ends of the second guide rail 148 are fixed on the fixed bracket 15, and the second slide block 149 is connected to the fixed bracket 15 or the X-ray light source 131 through a fastener.

Please refer to FIG. 8 to further understand that the mounting bracket 141 includes a light source mounting part 142, a first camera mounting part 144 and a mirror mounting part 143. Herein, the light source mounting part 142 is plate-shaped, and the middle position of one end of the light source mounting part 142 extends outwards to form a plate-shaped mirror mounting part 143 and a first camera mounting part 144 in turn. The X-ray light source 131 is fixed on the light source mounting part 142 by a fastener, the first camera 111 is fixed on the first camera mounting part 144, and the first mirror 112 is fixed on the mirror mounting part 143.

In this embodiment, the X-ray light source 131, the first camera 111 and the first mirror 112 are all located on the downward lower mounting surface of the mounting bracket 141. It is true that in other embodiments, as an alternative means, the X-ray light source 131, the first camera 111 and the first mirror 112 are all fixed on the upward upper mounting surface of the mounting bracket 141, which is also within the protection scope of the present disclosure.

Figure 10:
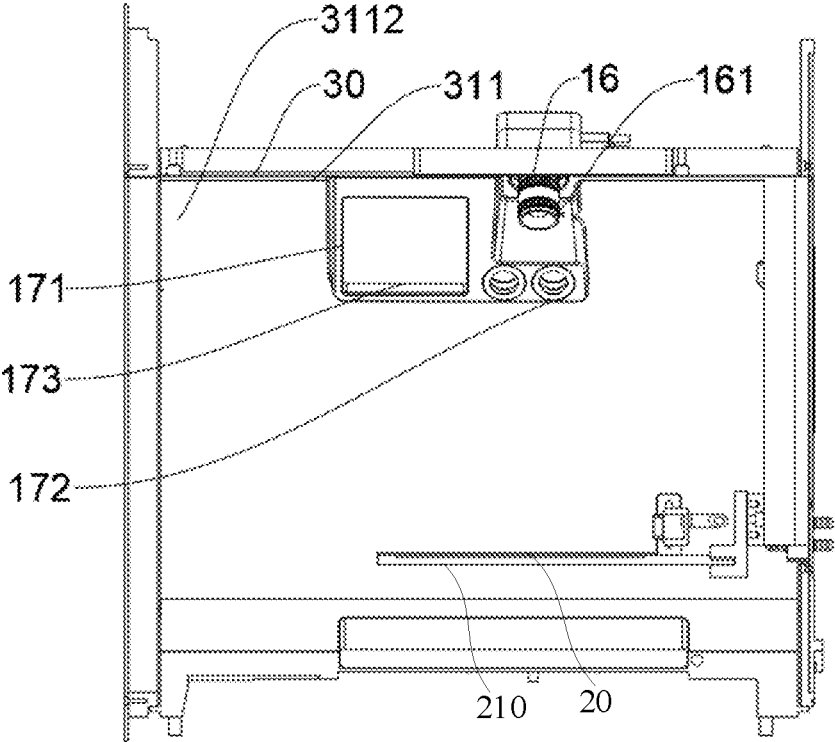
FIG. 10 is a structural diagram of the imaging system of an embodiment of the present disclosure.

Please refer to FIG. 10 for understanding. On the basis of any of the above embodiments, the camera unit 10 further includes a third imaging module 16, and the third imaging module 16 includes a third camera 161. The third camera 161 is directly or indirectly fixedly connected to the rotation unit 30, and is located at the accommodating cavity 3112. The third camera 161 is configured to directly receive light emitted or reflected by the sample 200.

Specifically, the third camera 161 performs imaging based on the principle of visible light imaging. The third camera 161 is directly or indirectly fixedly connected to the rotary support assembly 311. The third camera 161 and the sample 200 are located in the same space, and there are no other physical components for isolation, or the space where the third camera 161 is located is connected to the space where the sample 200 is located, and the light emitted or reflected by the sample 200 directly enters the third camera 161.

In the imaging system 100 of this embodiment, the first imaging module 11 uses an infrared camera, the second imaging module 12 uses a CCD camera, the third imaging module 16 uses a CMOS camera, and the X-ray imaging module 13 performs CT imaging based on X-ray imaging principles. The four imaging modules of the imaging system 100 in this embodiment are all based on different imaging principles to image the sample 200, and the operator selects the corresponding imaging module to operate according to the operation needs, so as to perform the subsequent operations of two-dimensional reconstruction, three-dimensional reconstruction and image fusion on the acquired image information, Please refer to FIGS. 10-11 for understanding. In the imaging system 100 of the embodiment of the present disclosure, the camera unit 10 further includes a first light source 171 for emitting a near-infrared laser. When the first camera 111 images, the first light source 171 illuminates the sample 200, and the excited light of the sample 200 enters the first mirror 112 through the first optical path 300, and is further reflected into the first camera 111, so as to realize infrared excitation imaging of the sample 200.

Please refer to FIGS. 10-11 for understanding. In the imaging system 100 of the embodiment of the present disclosure, the camera unit 10 further includes a second light source 172 for emitting laser. The second light source 172 is used for exciting the sample 200 to emit biological fluorescence. The biological fluorescence enters the second mirror 122 through the first optical path 300 and is further reflected into the second camera 121 to realize fluorescence imaging. The second light source 172 can emit excitation light of different wave bands, in other words, the second light source 172 can emit excitation light of different colors. According to the imaging requirements of the sample 200, the excitation light of the corresponding wave band is turned on, and the sample 200 is irradiated with the excitation light to generate biologically excited fluorescence.

It is one way of using the second imaging module 12 to achieve fluorescence imaging of sample 200 in cooperation with the second light source 172. As another way of using, the second imaging module 12 may also image the sample 200 that can generate biological fluorescence without excitation light, that is, the second light source 172 does not start, and the fluorescence emitted by the sample 200 itself enters the second imaging module 12 through the first optical path 300.

Please refer to FIG. 10 for understanding. In the imaging system 100 of the embodiment of the present disclosure, the camera unit 10 further includes a third light source for emitting white light. When the third camera 161 is imaging, the third light source illuminates the sample 200, and the light reflected by the sample 200 enters the third camera 161. It is true that the third light source is not only used in the imaging process of the third camera 161, but also can be used when white light is needed to illuminate the sample table unit 20 or to illuminate the inside of the accommodating cavity 3112.

In the embodiment of the present disclosure, the camera unit 10 is provided with a first light source 171, a second light source 172, and a third light source at the same time, and the second light source 172 and the third light source are realized through RGBW LED light source, and the first light source 171 is an excitation light source that emits infrared laser. The first light source 171, the second light source 172 and the third light source are directly or indirectly fixed inside a rotary box 42.

Please refer to FIG. 11 for understanding. The imaging system 100 of the embodiment of the present disclosure also includes a dark box unit, and the dark box unit includes an inner box module 40 located in the accommodating cavity 3112. The inner box module 40 is provided with a light-passing hole located on the first optical path 300, and the sample table unit 20 is located in the inner box module 3112. The light directly emitted by the sample 200 is incident to the outside of the inner box module 40 through the light-passing hole.

In other words, the inner box module 40 is hollow inside and forms an imaging room 41, and the sample table unit 20 is located in the imaging room 41. When the imaging system 100 images the sample 200, the inner box module 40 realizes the light transmission inside and outside of the imaging room 41 at the light-passing hole. The other positions of the imaging room 41 in the inner box module 40 are all optically sealed from the outside at other positions of the inner box module 40.

In the imaging system 100 of the embodiment of the present disclosure, the inner box module 40 includes a rotary box 42 and a fixed box 43. The rotary box 42 is set to remain relatively stationary with the rotation unit 30, and the fixed box 43 is rotatably connected with the rotary box 42 and optically sealed; the sample table unit 20 is fixedly connected to the fixed box 43 and penetrates into the rotary box 42.

In other words, the fixed box 43 and the sample table unit 20 are directly or indirectly fixed on the housing 400, and the rotary box 42 and the rotation unit 30 remain relatively stationary. During imaging, the rotation unit 30 drives the rotary box 42 to rotate with respect to the fixed box 43 to the imaging position, and the camera unit 10 receives the light transmitted from the sample 200 through the first optical path 300 or irradiates the sample 200 with X-rays through the first optical path 300. The above-mentioned imaging room 41 can be understood as being formed separately via the hollow rotary box 42, or formed together via the hollow rotary box 42 and the hollow fixed box 43.

In this embodiment, the fixed box 43 is a cylinder with one end open or both ends open; the rotary box 42 is a cylinder with one end open or both ends open. An opening of the rotary box 42 is slidably connected with an opening of the fixed box 43 in the circumferential direction, and the two are optically sealed at the connection to prevent the light outside the inner box module 40 from interfering with the imaging.

Figure 12:
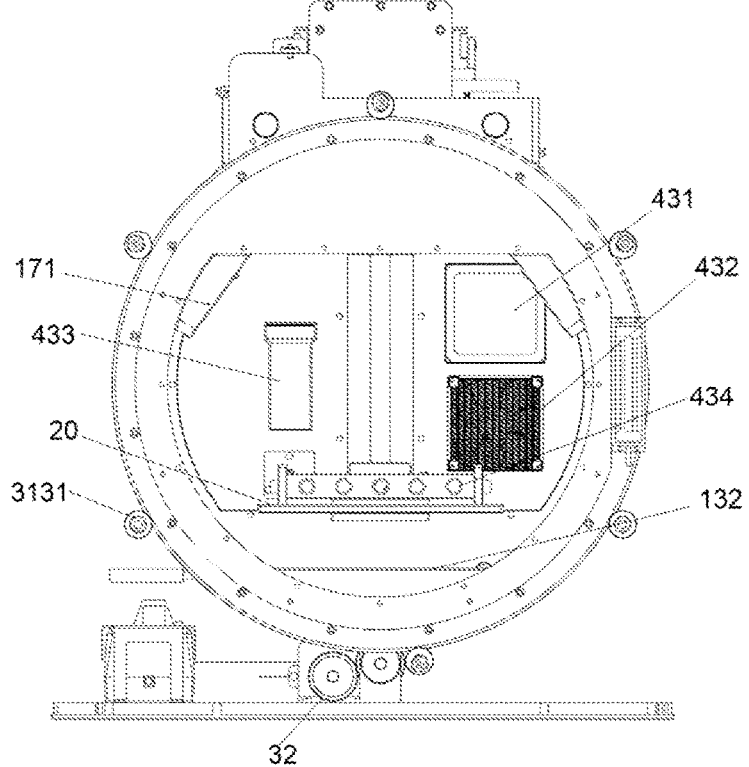
FIG. 12 is a structural diagram of the imaging system of an embodiment of the present disclosure.

Please refer to FIG. 12 for understanding. The fixed box 43 is provided with a temperature-controlled air inlet 431 for communicating with the outside and a temperature-controlled air outlet 432 for communicating with the outside. Herein, the imager 1000 where the imaging system 100 is located is provided with a temperature control system, and the temperature-controlled air inlet 431 and the temperature-controlled air outlet 432 are reserved through holes or slots for communicating with the temperature control system, so as to realize the temperature control of the imaging room 41 by the temperature control system.

Please refer to FIG. 12 for understanding. The fixed box 43 is also provided with an anesthesia air inlet for communicating with the outside and an anesthesia air outlet 434 for communicating with the outside. Herein, the imager 1000 where the imaging system 100 is located is provided with an anesthesia system, and the anesthesia inlet and the anesthesia outlet 434 are reserved through holes or slots for communicating with the anesthesia system. The anesthesia system is preferably applied in the imager 1000 capable of imaging the living animal sample 200.

Please refer to FIG. 12 for understanding. The fixed box 43 reserves a mounting position for an external humidifier 433 (not shown in the figure). It is true that in other embodiments, as an alternative means, the fixed box 43 is provided with a moisture inlet for communicating with the outside and a moisture outlet for communicating with the outside; the imager 1000 where the imaging system 100 is located is provided with a moisture control system, and the moisture inlet and moisture outlet are reserved through holes or slots for connecting the moisture control system so as to control the moisture in the imaging room 41.

Figure 13:
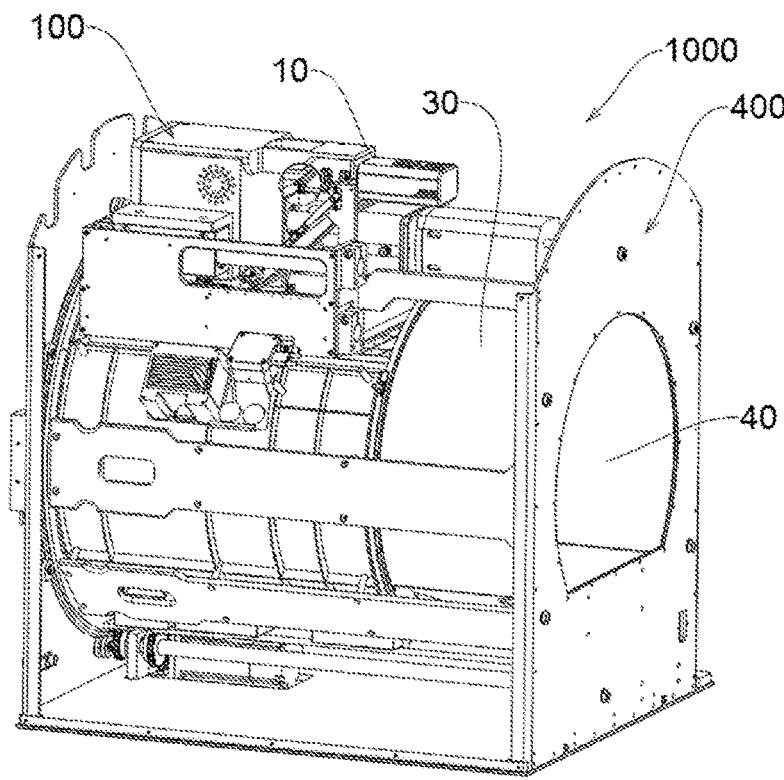
FIG. 13 is a structural diagram of a plant imager in an embodiment of the present disclosure.
Figure 14:
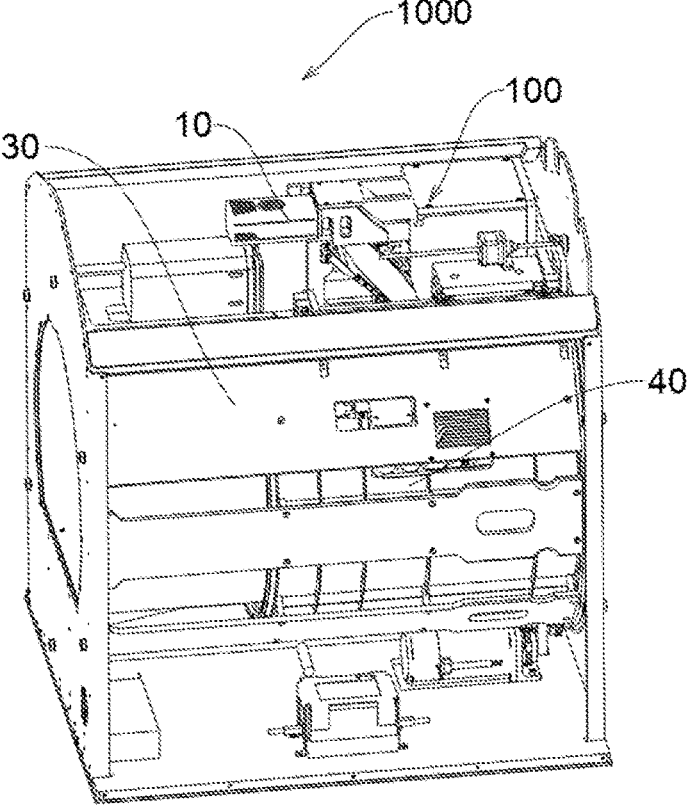
FIG. 14 is a structural diagram of an animal imager in an embodiment of the present disclosure.
Figure 15:
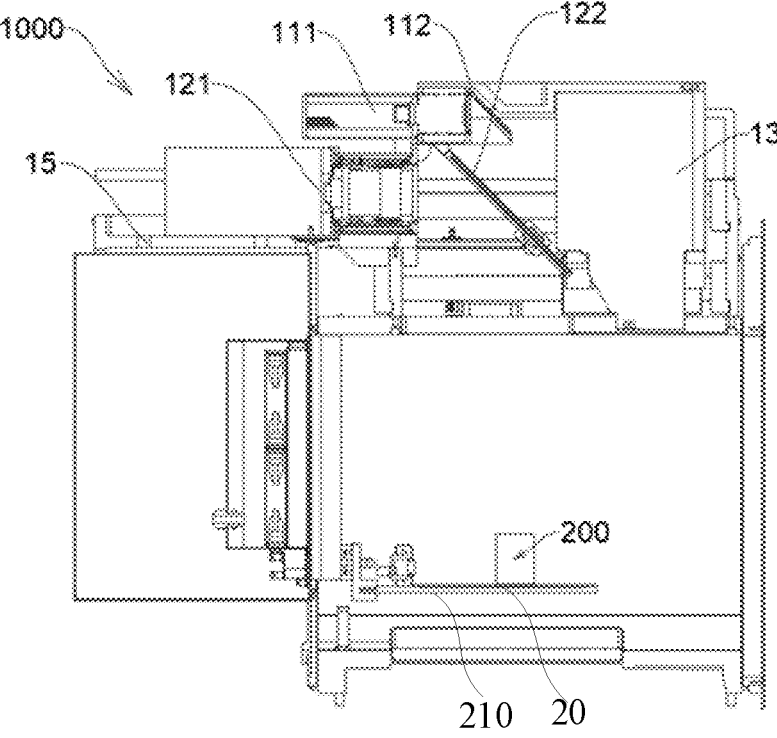
FIG. 15 is a structural diagram of an animal and plant imager in an embodiment of the present disclosure.

The imaging system 100 of any of the above-mentioned embodiments can be applied to different types of imagers 1000. Three types of imagers 1000 are briefly described below. FIGS. 13-15 illustrate a structural schematic of applying the imaging system 100 in the above embodiments to the imager 1000, and the imager 1000 shown in the figures may be any one of the following three types of imagers 1000. It is true that the imaging system 100 of the embodiment of the present disclosure is not limited to be applied to the following three types of imagers 1000.

The imager 1000 provided in the embodiment of the present disclosure is a plant imager for imaging a living plant, and the plant imager includes the imaging system 100 and the housing 400 in any of the above embodiments.

The plant imager of this embodiment and the imaging system 100 improve the accuracy of the acquired image information based on the same reason.

The imager 1000 provided in the embodiment of the present disclosure is an animal imager for imaging a living animal, and the animal imager includes the imaging system 100 and the housing 400 in any of the above embodiments.

The animal imager of this embodiment and the imaging system 100 improve the accuracy of the acquired image information based on the same reason.

The imager 1000 provided in the embodiment of the present disclosure is an animal and plant imager, including the imaging system 100 and the housing 400 in any of the above embodiments. The animal and plant imager has the functions of imaging animals and plants.

The animal and plant imager in this embodiment and the imaging system 100 improve the accuracy of the acquired image information based on the same reason.

Although the specific implementation of the present disclosure has been described above, those skilled in the art should understand that this is only an example, and the protection scope of the present disclosure is defined by the appended claims. Those skilled in the art can make various changes or modifications to these embodiments without departing from the principle and essence of the present disclosure, but these changes and modifications all fall within the protection scope of the present disclosure.

What is claimed is:

1. A rotary imaging system, comprising:
a sample table unit which is used for carrying a sample, comprising a sample table;
a camera unit which is used for imaging the sample; and,
a rotation unit, the rotation unit comprises an accommodating cavity accommodating the sample table unit, the rotation unit is used for driving the camera unit to rotate with respect to the sample table unit, and controlling the camera unit to be stationary with respect to the sample table unit;
the camera unit comprises a first imaging module and a second imaging module both arranged on the rotation unit; when the first imaging module performs imaging, a light emitted, excited or reflected by the sample enters the first imaging module through a first optical path; when the second imaging module performs imaging, a light emitted, excited or reflected by the sample enters the second imaging module through the first optical path;
the first imaging module comprises a first camera and a first mirror both arranged on the rotation unit, and the second imaging module comprises a second camera and a second mirror both arranged on the rotation unit;
when the first imaging module performs imaging, the second mirror is located at a first position, and the light emitted, excited or reflected by the sample enters the first mirror through the first optical path, and is reflected into the first camera by the first mirror;
when the second imaging module performs imaging, the second mirror is located at a second position, and the light emitted, excited and reflected by the sample enters the second mirror through the first optical path, and is reflected into the second camera by the second mirror;
the second imaging module also includes a swinging component, which is fixed on the fixed bracket by means of a fastener, the swinging component drives the second mirror to swing with respect to the second camera, and switches between the first position and the second position.

2. The rotary imaging system according to claim 1, wherein the rotation unit comprises a rotation module and a power module, and the power module is used for driving the rotation module to rotate with respect to the sample table unit; the rotating module is provided with the accommodating cavity, and the camera unit is fixedly connected to the rotation module.

3. The rotary imaging system according to claim 1, wherein the swinging component comprising:
a swing bracket, the swing bracket is rotatably connected with the second camera, and the second mirror is fixedly connected to the swing bracket;

a first sliding assembly, the first sliding assembly is fixedly connected to the swing bracket, and an output end of the first sliding assembly is slidably connected to the swing bracket; and,
a first linear mechanism, the first linear mechanism is fixedly connected to the rotation unit, an output end of the first linear mechanism is rotatably connected to the output end of the first sliding assembly; the output end of the first linear mechanism outputs a linear motion, driving the output end of the first slide assembly to slide with respect to the swing bracket, and causing the swing bracket to swing.

4. The rotary imaging system according to claim 1, wherein the camera unit further comprises:
an X-ray imaging module, the X-ray imaging module comprises an X-ray light source for emitting an X-ray and an X-ray detector, the X-ray detector is set to remain relatively stationary with the sample table unit, and when the X-ray imaging module performs imaging, the second mirror is located at the first position, the X-ray propagates along the first optical path, and the X-ray detector absorbs the X-ray passing through the sample and converts the X-ray into image information; and,
a synchronous motion driving part, the synchronous motion driving part is fixedly connected to the rotation unit and used for driving the X-ray light source and the first imaging module to move synchronously.

5. The rotary imaging system according to claim 4, wherein the synchronous motion driving part comprises:
a mounting bracket, the mounting bracket is fixedly connected to the rotation unit, and the X-ray light source, the first camera and the first mirror are all fixedly connected to the mounting bracket; and,
a second linear mechanism, the second linear mechanism is connected to the rotation unit and used for driving the mounting bracket to move in a horizontal direction.

6. The rotary imaging system according to claim 5, wherein the second linear mechanism comprises:
a second drive assembly, the second drive assembly is fixedly connected to the rotation unit and used for driving the mounting bracket to move linearly; and,
a second sliding assembly, the second sliding assembly comprises a second guide rail and a second slide block in one-to-one correspondence, the second guide rail is fixedly connected to the rotation unit, and the second slide block is slidably connected with the second guide rail and fixedly connected with the mounting bracket.

7. The rotary imaging system according to claim 1, wherein the camera unit further comprises a third imaging module; the third imaging module comprises a third camera based on visible light imaging, and the third camera is fixedly connected to the rotation unit and located in the accommodating cavity; the third camera is configured to directly receive light emitted or reflected by the sample.

8. The rotary imaging system according to claim 7, wherein:
the first camera is an infrared camera; or,
the second camera is a bioluminescence camera or a fluorescence camera; or,
the third camera is a CMOS camera; or,
the camera unit comprises a first light source for emitting a near-infrared laser, and when the first camera is imaging, the first light source illuminates the sample; or,
the camera unit comprises a second light source for emitting an excitation light, the second light source excites the sample to emit biological fluorescence, and the biological fluorescence enters the second imaging module through the first optical path for imaging; or, the camera unit comprises a third light source for emitting a white light, and when the third camera is imaging, the third light source illuminates the sample.

9. The rotary imaging system according to claim 1, wherein the rotary imaging system further comprises a dark box unit, the dark box unit comprises an inner box module located in the accommodating cavity, and the inner box module is provided with a light-passing hole, the light-passing hole is located on the first optical path, the sample table unit is located in the inner box module, and the light emitted, excited and reflected by the sample is incident to the outside of the inner box module through the light-passing hole.

10. The rotary imaging system according to claim 9, wherein the inner box module comprises:

a rotary box, the rotary box is set to keep relatively stationary with the rotation unit, the rotary box is provided with the light-passing hole; and, a fixed box, the fixed box is rotatably connected with the rotary box and optically sealed; the sample table unit is fixedly connected to the fixed box, and penetrated into the rotary box.

11. The rotary imaging system according to claim 10, wherein the fixed box is a cylinder; or, the rotary box is a cylinder; or, the fixed box is provided with a temperature-controlled air inlet for communicating with outside and a temperature-controlled air outlet for communicating with the outside; or, the fixed box is provided with an anesthesia air inlet for communicating with the outside and an anesthesia air outlet for communicating with the outside; or, the fixed box is provided with a moisture air inlet for communicating with the outside and a moisture air outlet for communicating with the outside.

12. A plant imager, comprising a housing, the sample is a living plant, wherein the plant imager also comprises the imaging system according to claim 1, and the rotation unit is connected to inner of the housing.

13. An animal imager, comprising a housing, the sample is a living animal, wherein the animal imager also comprises the imaging system according to claim 1, and the rotation unit is connected to inner of the housing.

14. An animal and plant imager, comprising a housing, and the animal and plant imager has functions of imaging a living animal and imaging a living plant; wherein, the animal and plant imager also comprises the imaging system according to claim 1, and the rotation unit is arranged inside the housing.

15. A rotary imaging system, comprising:

a sample table unit which is used for carrying a sample, comprising a sample table;

a camera unit which is used for imaging the sample; and, a rotation unit, the rotation unit comprises an accommodating cavity accommodating the sample table unit, the rotation unit is used for driving the camera unit to rotate with respect to the sample table unit, and controlling the camera unit to be stationary with respect to the sample table unit;

the camera unit comprises a first imaging module and a second imaging module both arranged on the rotation unit; when the first imaging module performs imaging, a light emitted, excited or reflected by the sample enters the first imaging module through a first optical path;

when the second imaging module performs imaging, a light emitted, excited or reflected by the sample enters the second imaging module through the first optical path;

the first imaging module comprises a first camera and a first mirror both arranged on the rotation unit, and the second imaging module comprises a second camera and a second mirror both arranged on the rotation unit;

when the first imaging module performs imaging, the second mirror is located at a first position, and the light emitted, excited or reflected by the sample enters the first mirror through the first optical path, and is reflected into the first camera by the first mirror;

when the second imaging module performs imaging, the second mirror is located at a second position, and the light emitted, excited and reflected by the sample enters the second mirror through the first optical path, and is reflected into the second camera by the second mirror;

the second imaging module also includes a swinging component, which is fixed on the fixed bracket by means of a fastener, the swinging component drives the second mirror to swing with respect to the second camera, and switches between the first position and the second position;

a sample table unit which is used for carrying a sample, comprising a sample table (201);

the rotation unit comprises a rotation module and a power module, and the power module is used for driving the rotation module to rotate with respect to the sample table unit; the rotating module is provided with the accommodating cavity, and the camera unit is fixedly connected to the rotation module;

the rotation module comprises:

a rotary support assembly, the rotary support assembly is provided with the accommodating cavity, and the camera unit is installed on the rotary support assembly;

a circular guide rail, both ends of the rotary support assembly are fixedly connected to the circular guide rail; and, a guide assembly, the guide assembly is used for guiding the circular guide rail, and making the circular guide rail be located on a preset circular track.

16. The rotary imaging system according to claim 15, wherein the guide assembly comprises several pulleys, each of the pulleys in the same guide assembly is evenly distributed along a virtual circle, and the pulleys guide the circular guide rail so that the circular guide rail is located on the preset circular track.

17. The rotary imaging system according to claim 16, wherein each of the guide assemblies is provided with 6 pulleys; or, the guide assembly guides at least one of an outer ring and the outer ring of the circular guide rail.

18. The rotary imaging system according to claim 15, wherein the rotary support assembly comprises a connecting piece, both ends of the connecting piece are fixedly connected to the circular guide rail, and the camera unit is installed on the connecting pieces; wherein:

the rotary support assembly is provided with several plate-shaped connecting pieces, each of the connecting pieces is arranged at intervals along the circumferential direction of the circular guide rail, and each connecting piece surrounds to form the accommodating cavity; or, the rotary support assembly is provided with several circular connecting pieces, each connecting piece is arranged at intervals along the axial direction of the circular guide rail, adjacent connecting pieces are connected, and the middle part of each connecting piece forms the accommodating cavity, and connecting pieces located at two ends are fixedly connected with the circular guide rail; or, the rotary support assembly is provided with one connecting piece, and the connecting piece is provided with the accommodating cavity.

19. The rotary imaging system according to claim 15, wherein the circular guide rail comprises a guide rail part and a connecting part; the connecting part is in a shape of an annular plate or a cylinder; at least one of the inner ring and the outer ring of the connecting part is provided with the guide rail part; the rotary support assembly is fixedly connected to the connecting part; or, the circular guide rail comprises a transmission gear part, the transmission gear part meshes with the power module, and the power module makes the circular guide rail rotate by driving the transmission gear part.

20. A rotary imaging system, comprising:

a sample table unit which is used for carrying a sample, comprising a sample table;

a camera unit which is used for imaging the sample; and, a rotation unit, the rotation unit comprises an accommodating cavity accommodating the sample table unit, the rotation unit is used for driving the camera unit to rotate with respect to the sample table unit, and controlling the camera unit to be stationary with respect to the sample table unit;

the camera unit comprises a first imaging module and a second imaging module both arranged on the rotation unit; when the first imaging module performs imaging, a light emitted, excited or reflected by the sample enters the first imaging module through a first optical path; when the second imaging module performs imaging, a light emitted, excited or reflected by the sample enters the second imaging module through the first optical path;

the first imaging module comprises a first camera and a first mirror both arranged on the rotation unit, and the second imaging module comprises a second camera and a second mirror both arranged on the rotation unit;

when the first imaging module performs imaging, the second mirror is located at a first position, and the light emitted, excited or reflected by the sample enters the first mirror through the first optical path, and is reflected into the first camera by the first mirror;

when the second imaging module performs imaging, the second mirror is located at a second position, and the light emitted, excited and reflected by the sample enters the second mirror through the first optical path, and is reflected into the second camera by the second mirror;

the second imaging module also includes a swinging component, which is fixed on the fixed bracket by means of a fastener, the swinging component drives the second mirror to swing with respect to the second camera, and switches between the first position and the second position;

a sample table unit which is used for carrying a sample, comprising a sample table (201);

the rotation unit comprises a rotation module and a power module, and the power module is used for driving the rotation module to rotate with respect to the sample table unit; the rotating module is provided with the accommodating cavity, and the camera unit is fixedly connected to the rotation module;

the power module comprises a power element for output a torque and a gear set, an input end of the gear set is fixedly connected to an output end of the power element, and an output end of the gear set meshes with the rotation module.

\* \* \* \* \*